United States Patent
Teeny et al.

(10) Patent No.: US 9,005,208 B2
(45) Date of Patent: Apr. 14, 2015

(54) LIGAMENT BALANCING FEMORAL TRIAL

(71) Applicant: Howmedica Osteonics Corp., Mahwah, NJ (US)

(72) Inventors: Steven Teeny, Big Harbor, WA (US); Scott Logan, Ringwood, NJ (US); Gearoid Walsh, County Clare (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 231 days.

(21) Appl. No.: 13/781,040

(22) Filed: Feb. 28, 2013

(65) Prior Publication Data

US 2014/0243835 A1    Aug. 28, 2014

(51) Int. Cl.
| | | |
|---|---|---|
| A61B 17/58 | (2006.01) | |
| A61B 17/60 | (2006.01) | |
| A61F 2/00 | (2006.01) | |
| A61B 17/15 | (2006.01) | |

(52) U.S. Cl.
CPC .................................. A61B 17/155 (2013.01)

(58) Field of Classification Search
USPC .................................................. 606/86 R–90
See application file for complete search history.

(56) References Cited

U.S. PATENT DOCUMENTS

| | | |
|---|---|---|
| 4,401,112 A | 8/1983 | Rezaian |
| 5,423,827 A | 6/1995 | Mumme et al. |
| 5,776,137 A | 7/1998 | Katz |
| 6,022,377 A | 2/2000 | Nuelle et al. |
| 6,056,756 A | 5/2000 | Eng et al. |
| 6,077,270 A * | 6/2000 | Katz ................................. 606/88 |
| 7,087,055 B2 | 8/2006 | Lim et al. |
| 7,455,647 B2 | 11/2008 | Tarabichi |
| 7,635,369 B2 | 12/2009 | Cinquin et al. |
| 7,651,500 B2 | 1/2010 | Supper et al. |
| 2006/0149277 A1 | 7/2006 | Cinquin et al. |
| 2006/0235423 A1 | 10/2006 | Cantu |
| 2006/0241643 A1 | 10/2006 | Lim et al. |
| 2007/0173851 A1 | 7/2007 | McMillen et al. |
| 2007/0233140 A1 | 10/2007 | Metzger et al. |
| 2008/0161824 A1 | 7/2008 | McMillen |
| 2009/0222089 A1 | 9/2009 | Hauri et al. |
| 2010/0249788 A1 | 9/2010 | Roche |
| 2010/0249790 A1 | 9/2010 | Roche |
| 2010/0249791 A1 | 9/2010 | Roche |

OTHER PUBLICATIONS

DePuy, LCS Surgical Technique, 2008.

* cited by examiner

*Primary Examiner* — Sameh Boles
(74) *Attorney, Agent, or Firm* — Lerner, David, Littenberg, Krumholz & Mentlik, LLP

(57) ABSTRACT

An instrument for setting ligament tension between a distal femur and a proximal tibia has a rod mounted on a femur. The rod has an extension extending along a first axis. A first drive element is mounted on the distal femur and is rotatable about a second axis. A body is rotatably mounted on the rod extension for rotation about the first axis. The body has a second drive element engaging the first drive element and a third drive element extending about a third axis offset from the first and second axes. A ligament tensioning element is mounted on the body and has a foot for engaging a posterior condyle of a femur and has a fourth drive element. A fifth drive element engages both the third and fourth drive elements for moving the ligament balancer with respect to the body along the third axis.

17 Claims, 17 Drawing Sheets

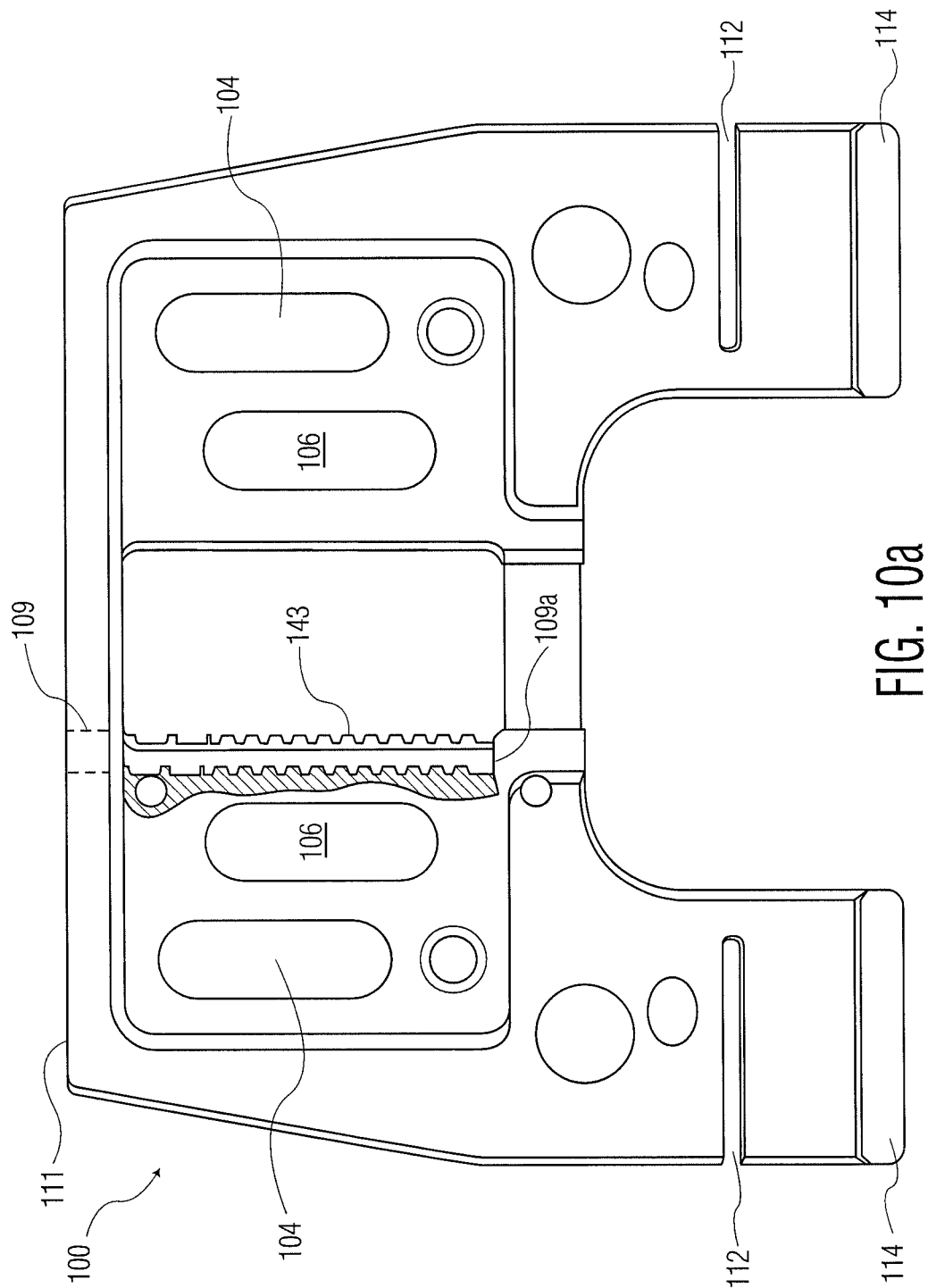

LIGAMENT BALANCING FEMORAL TRIAL

BACKGROUND OF THE INVENTION

The present invention relates generally to the implant of prosthetic joints and pertains, more specifically, to the preparation of the distal femur for the implant of a femoral knee prosthesis, utilizing a femoral guide, such as a femoral sizing guide for the subsequent location of a femoral cutting guide, to assist in establishing the surfaces necessary for locating and securing the prosthesis in place on the femur. More particularly, the invention relates to an instrument that allows the assessment of the balance of the knee ligaments by using a trial femoral condylar portion having a constant radius and an internal/external rotation adjustment mechanism as well as an anterior-posterior adjustment mechanism.

The implant of a prosthetic knee joint requires that the distal femur be prepared to receive the femoral component of the knee prosthesis by cutting the bone of the femur to establish accurately located surfaces against which the femoral knee prosthesis will rest upon implantation of the femoral component. Various guides are available to the surgeon for assisting in guiding a saw blade during use of the saw blade to make the femoral cuts which establish the desired surfaces. These guides usually are located and secured on the distal femur, often upon a transverse surface established initially at the distal femur, to provide guide surfaces for guiding the saw blade during the execution of an axially directed anterior femoral cut, an axially directed posterior femoral cut, an anterior chamfer and a posterior chamfer, all specifically related to the size of the femoral knee prosthesis to be implanted and to the position and orientation of the femoral knee prosthesis at the site of the implant. The appropriate location of a femoral cutting guide, then, generally requires the use of a femoral sizing guide to determine the size of the femoral knee prosthesis which will be implanted at an implant site in a particular recipient, and to locate the corresponding femoral cutting guide appropriately on the transverse distal femoral surface for proper placement of the femoral knee prosthesis upon implant at the implant site.

Femoral knee prostheses are made available in a range of standard sizes. A femoral sizing guide is used to assist in the selection of a standard size femoral knee prosthesis which will best fit the requirements of a particular implant site. Once selected, the femoral knee prosthesis must be located and oriented so as to attain appropriate rotational alignment and create a symmetric flexion gap.

The femoral component is typically a metallic alloy construction (e.g., cobalt-chrome alloy or 6A4V titanium alloy) and provides medial and lateral condylar bearing surfaces of multi-radii or constant radius design of similar shape and geometry as the natural distal femur.

One important aspect of the known component implantation procedures is the correct resection of the distal femur and proximal tibia. These resections must provide planes which are correctly oriented in order to properly accept the prosthetic components. Among the factors that are considered when assessing resection of the distal femur and proximal tibia are the proximal-distal location of the resection planes, the varus-valgus angle of the planes, and the change in relative orientation of the planes in response to change in flexion-extension angle of the knee.

Moreover, following distal resection the femur is shaped with the aid of a cutting block. To ensure correct shaping of the femur, the cutting block must be correctly positioned and sized. More specifically, the cutting block must be correctly positioned with respect to the anterior-posterior direction and must be correctly rotated about an axis perpendicular to the distal resection plane such that the block's rotation corresponds to the correct Internal/External (I/E) rotation of the femur relative to the tibia. The I/E rotation may be set in a number of ways. One way of setting I/E rotation is by referencing the angle formed between the cutting block's medial-lateral axis as projected onto the distal resection plane and the knee's posterior condylar axis as projected onto the distal resection plane. In a typical case, the angle formed between the cutting block's medial-lateral axis as projected onto the distal resection plane and the knee's posterior condylar axis as projected onto the distal resection plane is set to approximately 3 degrees and matches the angle formed between the epicondylar axis as projected onto the distal resection plane and the posterior condylar axis as projected onto the distal resection plane.

In addition, the cutting block should be correctly positioned with respect to the medial-lateral direction. However, medial-lateral positioning of the block is not as critical to the femur shaping procedure and, as such, does not require the same degree of precision as exercised during anterior-posterior positioning of the block and I/E rotation of the block.

A typical cutting block includes two or more fixation pegs, or "pins" that are used for positioning the block on the distal resection plane and securing the block to the plane. In practice, the block to be used is known and thus the positions of the pins within the block are known. Therefore, one can set the block's position in space by setting the pins' position in space. Accordingly, to position the block on the distal plane the appropriate pin positions are determined, pinholes are drilled at the determined positions, the pins in the block are lined up with the pinholes, and the pins are inserted into the pinholes to secure the block to the femur.

In many cases, the appropriate cutting block and the correct pinhole positions are determined using an instrument referred to as an "Anterior-Posterior Sizer" (or "AP Sizer"). The Sizer is designed to determine the appropriate cutting block and correct pinhole positions based on the type and size of femoral component that will be implanted. For example, the implant could be from the line of implants associated with the Stryker® Triathlon® Knee System which includes femoral implants of sizes 1-8. In such context, the AP Sizer will determine the size of Triathlon® implant that is needed and will indicate where the pinholes should be located for a cutting block corresponding to the Triathlon® implant of the determined size.

BRIEF SUMMARY OF THE INVENTION

The instrument of the present invention allows the assessment of the balance of the ligaments by means of a single radius on the external geometry of the tensioning element. The design of the instrument allows internal/external rotation of the device to be adjusted by means of an Allen key in combination with a gear mechanism. The device allows the anterior-posterior (AP) adjustment of the instrument by means of a hexagonal key in combination with an Acme Screw.

Once the desired position has been achieved, the instrument can be secured to the femur. A plate is positioned on the proximal tibia, and a trial reduction is performed. This is done by means of the single radius on the periphery of the instrument. The surgeon assesses stability throughout the complete range of motion. If required, the surgeon has the ability to open screws, make further adjustments (I/E rotation and/or AP Adjustment), secure the instrument in place again, and assess the stability again. Once the desired position of the instrument has been achieved, the instrument can be finally secured in position and the pin or peg holes drilled. The device also allows for the AP sizing of the femur for the correct implant size.

In the surgical method for using the instrument of the present invention, the surgeon inserts an intramedullary (IM) rod into the hole drilled in the femoral canal. The IM rod has a portion protruding distally from the resected distal femur. The surgeon then assembles distal plate on to the distal femur over the IM rod. The surgeon sets the distal plate at the approximate internal/external rotation position. The plate is then secured to the distal femur by means of two bone screws. The main body of the instrument is then placed over distal plate. The medial and lateral posterior feet on the main body are placed under the posterior condyles. The main body is secured to the distal plate by means of two screws. These two screws secure the main body to the distal plate, but still allow the main body to move in an AP direction by means of an adjustment screw. The surgeon performs a trial reduction with the instrument in place.

Trial reduction takes place by means of the offset single radius on the outer periphery of the posterior feet of the instrument main body device. The surgeon places tibial shim plate (2 mm or 4 mm thick) on the proximal tibia. This plate acts as a protective plate for the resected bone on the tibia, and also as a firm surface for rotation of the outer profile on the main body. The surgeon puts the knee through a range of motion and assesses stability throughout the complete range. The surgeon has multiple thickness spacer blocks which allow the surgeon to assess the gap (if any) on each condyle.

If the surgeon establishes that adjustment is required, then the following steps can be taken. If internal/external rotation is required, then the surgeon opens the two bone screws on the distal plate and places a hex key into centre screw mechanism and rotates the distal plate until the desired position has been obtained. The surgeon can secure the distal plate at this stage if desired. However, he can if he wishes adjust the AP position by means of the actuating screw. This is adjusted by means of a hex key placed onto the screw. Once the desired position has been achieved, then distal plate is secured to the femur.

The surgeon begins the process of assessing the resection levels and femoral component size. The resection level is assessed by means of a blade runner placed into the slots on the posterior side of the instrument. Two AP sizing stylus receiving holes exist on the medial and lateral sides of the main body. The femoral stylus is inserted into one of the holes. The stylus works by placing a tip of the stylus on the anterior cortex of the femur and an indicator line on the rod, indicates the size of femur on the main body by means of a scale.

Finally the surgeon drills two holes on the distal femur which ultimately position a standard 4-in-1 cutting guides in the correct position, which cutting guide directs an oscillating saw to make the standard anterior and posterior skim cuts and anterior and posterior chamfer cuts on the distal femur.

The above described instrument and method of use is accomplished by an instrument system for setting ligament tension between a distal femur and a proximal tibia during total knee arthroplasty. The instrument has an IM rod for mounting in an intramedullary canal of a distal femur, the rod having a portion extending outwardly of the distal femur along a first axis. A first drive elements is mounted on the rod portion extending from the distal femur and is rotatable about a second axis parallel to and offset from the first axis. A body is rotatably mounted on the extension portion of the rod for rotation about the first axis. The body has a second drive element engaging the first drive element whereby rotation of the first drive element about the second axis rotates the body with respect to the first axis. The body further comprising a third drive element extending about a third axis offset from the first and second axis. A ligament tensioning element is mounted on the body for movement with respect thereto. The ligament tensioning element has a foot for engaging a posterior condyle of a femur and having a fourth drive element extending generally parallel to and spaced from the third drive element; and a fifth drive element engaging both the third and fourth drive elements for moving the ligament tensioning element with respect to the body along the third axis.

The first drive element is a gear having teeth meshing with teeth on the second drive element. The third and fourth drive elements are a plurality of teeth and the fifth drive element is a screw operatively engaging the teeth. The ligament tensioning element has a first foot for engaging a posterior surface of a medial condyle and a second foot for engaging a lateral condyle of a femur. The first and second feet have outer surfaces for contacting a tibial surface, the outer surfaces having a portion with a constant radius in a saggital plane. The body includes first and second elongated slots elongated along an axis parallel to the third axis.

The instrument system as set forth in claim 6, wherein the system further comprises a pair of screws extending through the first and second slots of the body for mounting the body to a planar surface on the distal femur. The body also includes a first threaded bore on a medial side of the body and a second threaded bore on a lateral side of the body. The ligament tensioning element has first and second elongate openings respectively aligned with the first and second threaded bores in the body, and the system further comprises first and second screws extending respectively through the first and second slots and threaded into the first and second bores for mounting the ligament tensioning element to the body.

The elongated slots have elongated portions extending along axes parallel to the third axis.

The instrument further comprises a femoral sizing module mounted on the ligament balancer, the femoral sizing module moveable in an anterior-posterior direction with respect to the balancer and stylus slidably mounted on the module for movement in a proximal distal direction and the stylus having a tip for contacting an anterior surface of the distal femur.

Another aspect of the invention includes an instrument system for setting ligament tension between a distal femur and a proximal tibia during total knee arthroplasty. The instrument comprises a plate which is rotatably mounted on a resected planar distal surface of a femur for rotation about a first axis. A ligament tensioning element is mounted on the plate for rotation therewith about the first axis and for movement with respect to the plate in a plane parallel to the resected planar surface of the femur. The plate has a foot or feet for engaging a posterior surface of the distal femur. A device is provided for rotating the plate and ligament tension about the first axis. A system is provided for moving the tensioning element with respect to the plate in the plane in a generally anterior-posterior direction of the distal femur. Elements for locking the ligament tensioning element in a desired location with respect to the distal femur.

The instrument further comprises an intramedullary rod having a first portion aligned with a longitudinal axis of the femur and a second portion angled with respect to the first portion extending along the first axis.

The angle between the first and second rod portions, i.e., the longitudinal axis of the femur and the first axis is between 3° and 6°. The second portion comprises anti-rotation elements extending radically outwardly from the first axis. The system for rotating the plate and ligament about the first axis comprises a gear body having a bore engaging the second portion of the rod. The bore has a central axis coaxial with the first axis and a gear element rotatable with respect to the gear body about a third axis parallel to the first axis. The gear element having teeth operatively engaging a portion of the plate having teeth.

The plate includes an opening for receiving the gear body, this opening sized to permit the plate to rotate ±5° about a saggital plane bisecting the resected distal femur.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

FIG. 10a shows a rear view of the ligament tensioning element of FIG. 10 including an ACME screw mounted therein;

DETAILED DESCRIPTION

Figure 1:
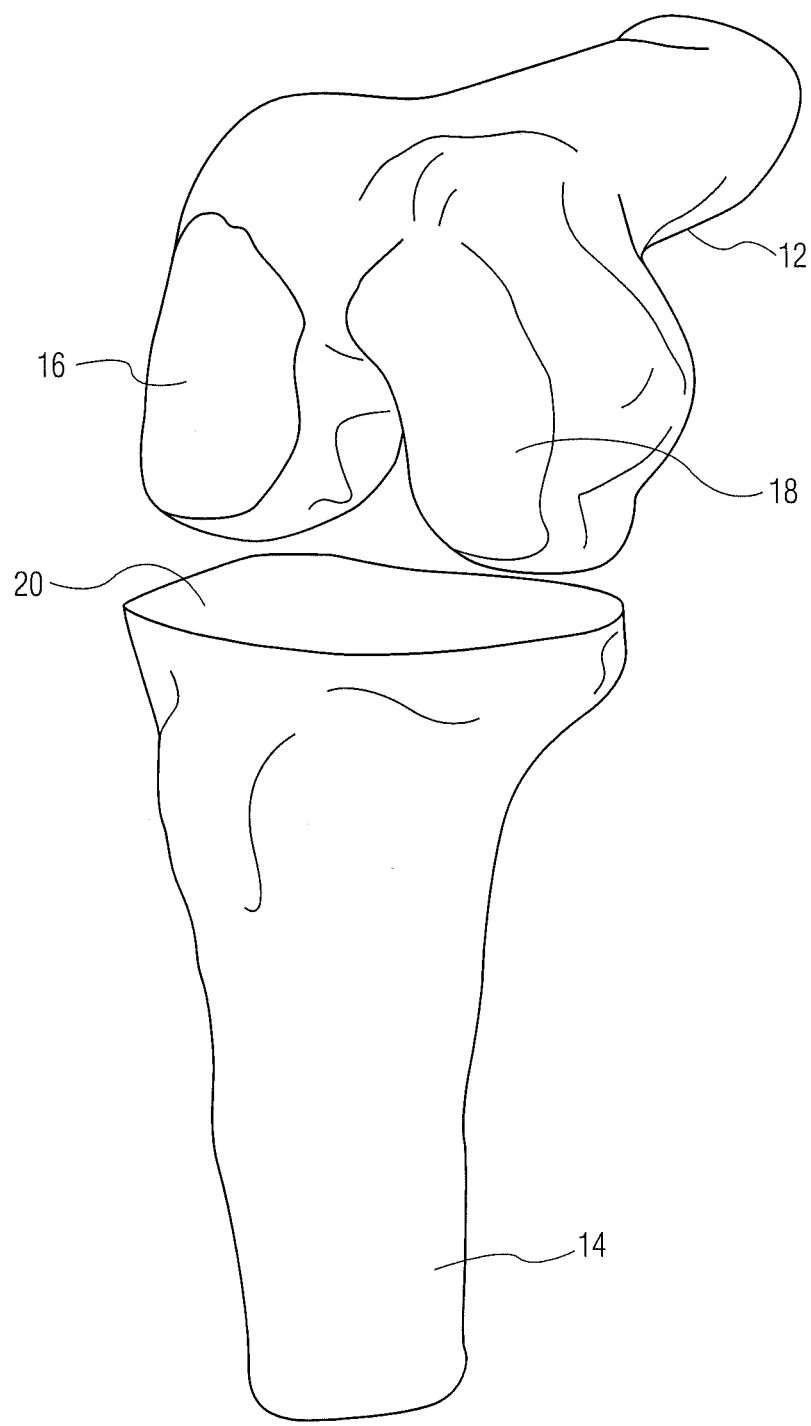
FIG. 1 is a perspective view of a femur and a tibia after having their respective distal and proximal surfaces resected to form planar cuts.

Referring to FIG. 1, there is shown a perspective view of a femur 12 and a tibia 14. Femur 12 includes two planar resected distal condylar surfaces 16 and 18 respectively. Tibia 14 includes a proximal planar cut surface 20 which will eventually receive a prosthetic tibial component (not shown).

Figure 2:
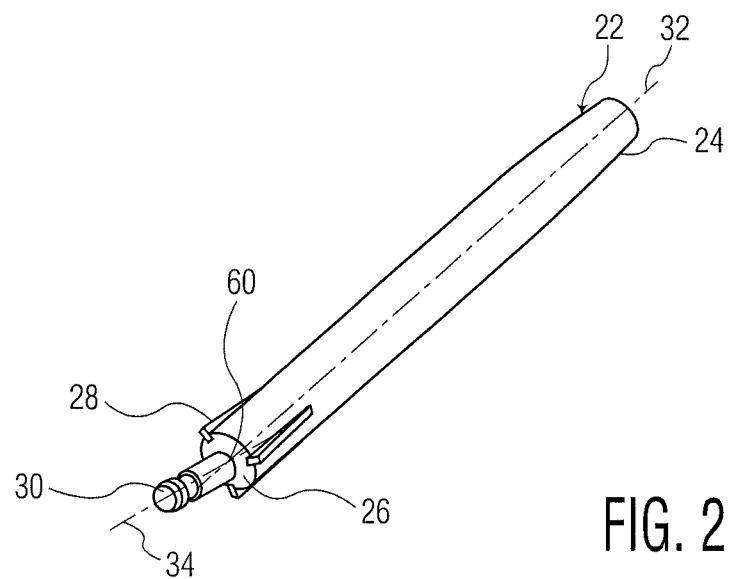
FIG. 2 is a perspective view of an intramedullary rod element for insertion into the intramedullary canal of the resected femur of FIG. 1.
Figure 3:
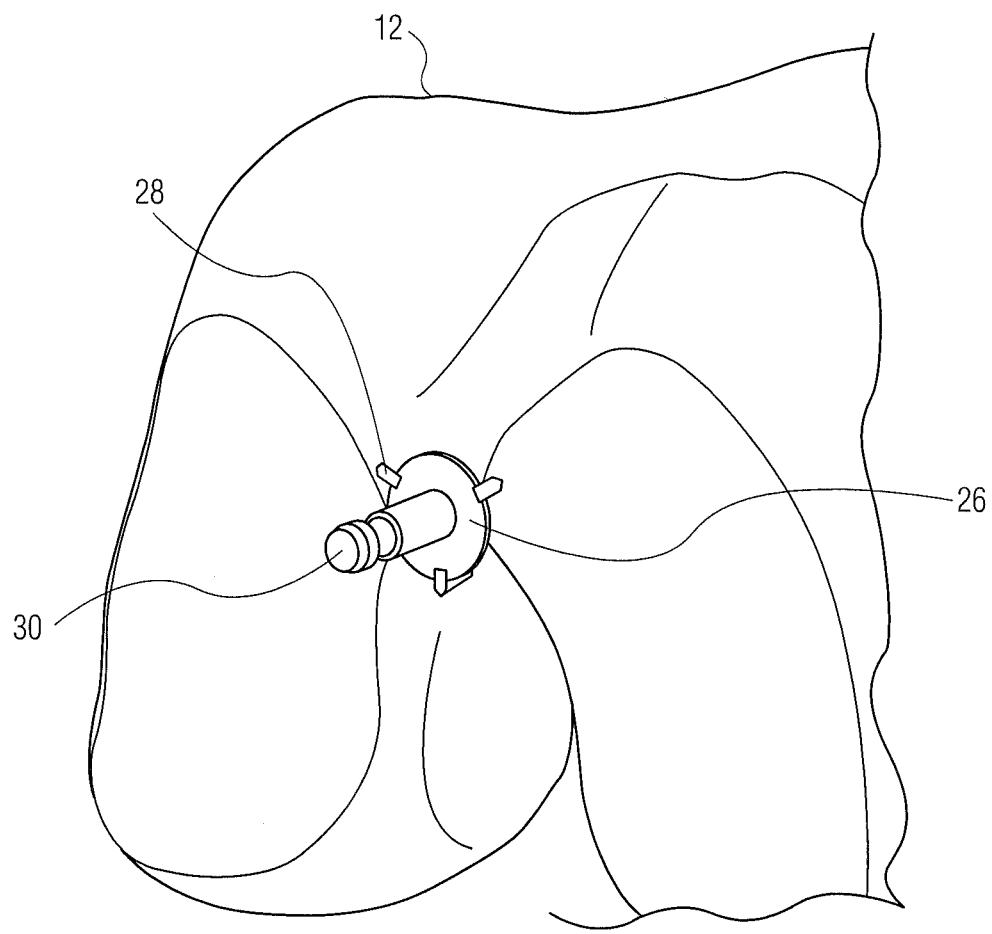
FIG. 3 shows the intramedullary rod element of FIG. 2 inserted in the distal femur of FIG. 1.

Referring to FIG. 2 there is shown an intramedullary rod 22 having a tip 24 for insertion into the femoral medullary canal and having a distal end 26 including three fins 28 preferably located at 120° increments about the outer circumference of distal end 26. Fins 28 are blade-like in form and will prevent rotation of rod 22 within the intramedullary canal. Distal end 26 includes a mounting rod 30, which, when rod 22 is placed in the canal, will extend distally beyond the planes of surfaces 16 and 18. The intramedullary rod 22 extends along an axis 32 with projection 30 extending along an axis 34. Preferably there is an angle of between 3 and 6° between axes 32 and 34 to compensate for the angle between the anatomic axis of the femur and the mechanical axis of the femur. FIG. 3 shows intramedullary rod 22 of FIG. 2 mounted in femur 12. As shown, fins 28 may be either internally formed on end 26 of rod 22 or may be removably mounted thereon.

Figure 4:
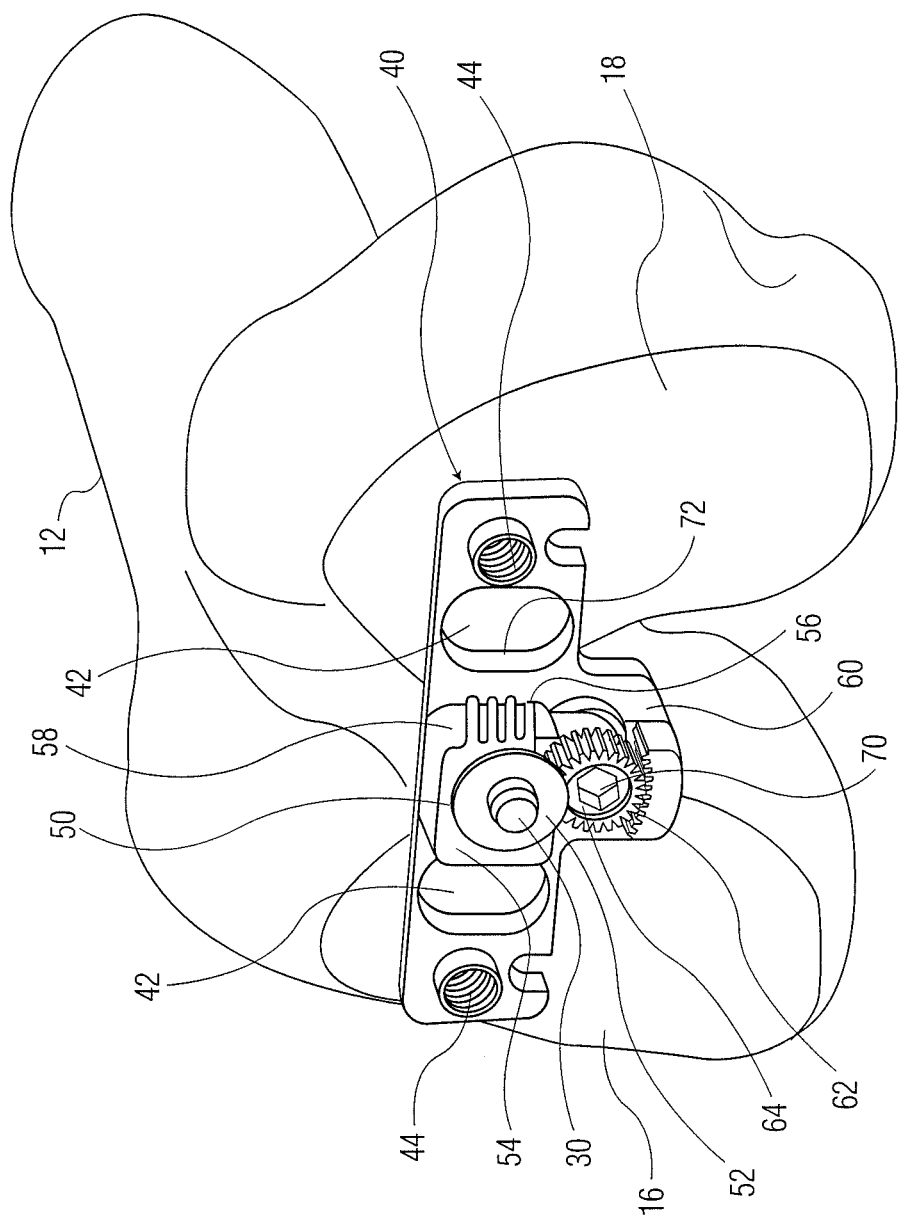
FIG. 4 shows a distal drive plate assembly mounted on a portion of the intramedullary rod element of FIG. 2, which extends beyond the distal surface shown in FIG. 1.
Figure 4A:
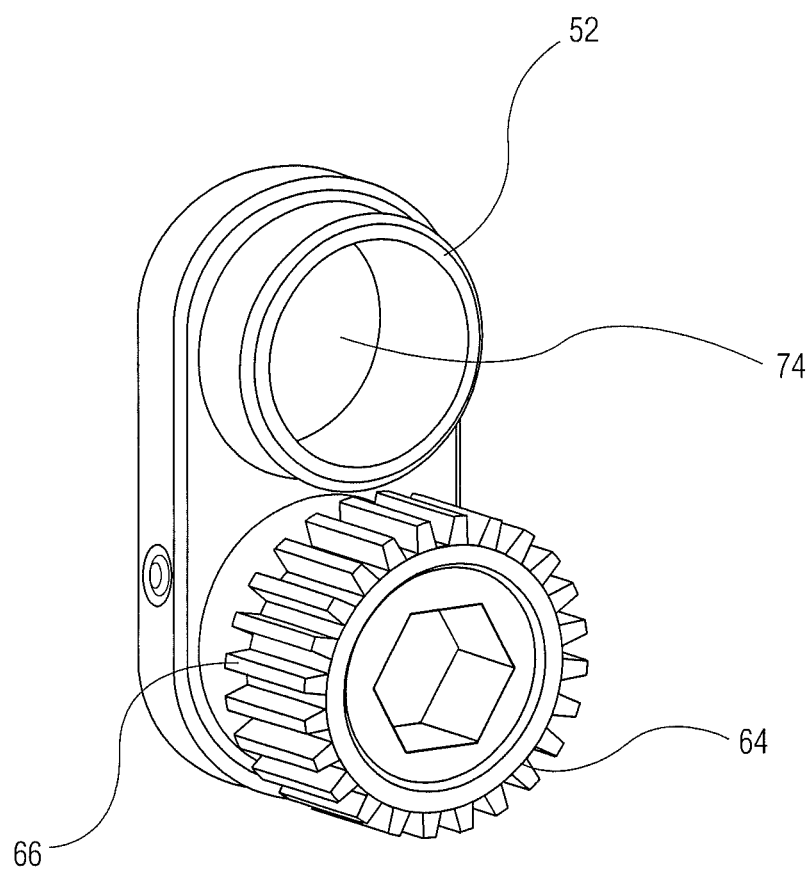
FIG. 4a is a detail of a modular bushing prior to being assembled to the plate of FIG. 4.
Figure 5:
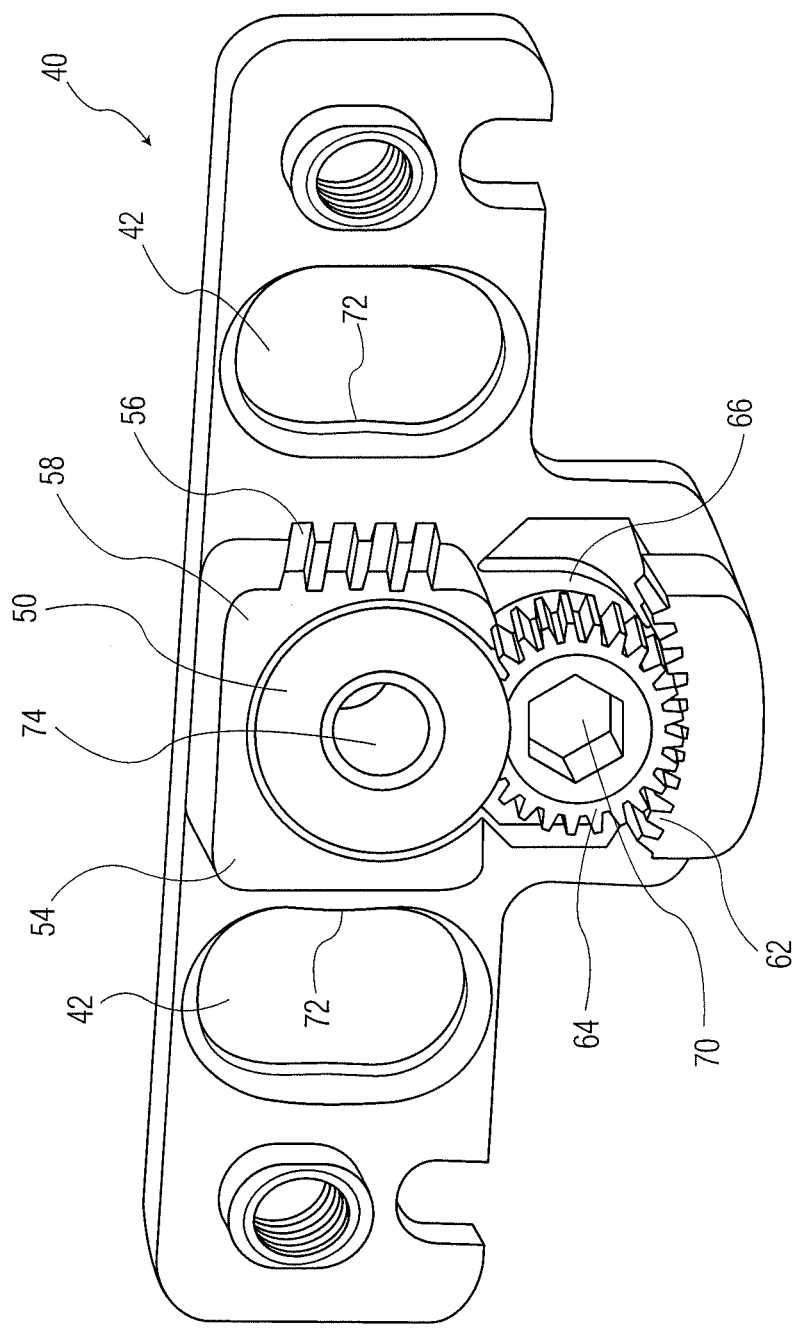
FIG. 5 is an enlarged perspective view of the drive plate shown in FIG. 4.

Referring to FIGS. 4, 4a and 5, there is shown distal plate 40 mounted on surfaces 16 and 18 in femur 12. Plate 40 includes a medial and a lateral slot 42 and a medial and lateral threaded mounting hole 44, which will receive ligament tensioning body mounting screws shown in FIGS. 8-13. Distal plate assembly 40 includes a central bore 50, which surrounds a bushing 52 for receiving end 30 of intramedullary rod 22. Bushing 52 includes a bore 74 for receiving end 30 of rod 22.

Bushing 52 is mounted within an opening in a square or rectangular boss 54 of distal plate assembly 40. Boss 54 has a series of rack gear tooth elements 56 formed on a medially facing side 58 of boss 54. As discussed below teeth 56 engage an ACME screw for adjusting the anterior-posterior position of a tensioning element body. Distal plate assembly 40 includes a posteriorly extending portion 60 which includes a curved gear element 62 adapted to engage a spur gear 64 mounted on an extension 66 of bushing 52, best seen in FIG. 5, on which spur gear 64 is freely rotatable. FIG. 4a shows bushing 52 prior to assembly on projection 30 and in boss 54. Typically bushing 52 is mounted on end 30 of rod 22 prior to mounting the distal plate assembly 40 on the distal femur. At assembly, spur gear 64 is slightly rotated such that the teeth thereof will mesh with the curved teeth elements 62 integrally formed on the distal plate assembly 40. Spur gear 64 includes a drive socket 70 which, in the preferred embodiment, is hexagonal in shape to receive a normal Allen wrench for rotating gear 64.

As shown in FIG. 5, slots 42 may have a kidney shape with a convex surface 72 facing outwardly from an axis through the center of the bore 74 in bushing 50.

Figure 6:
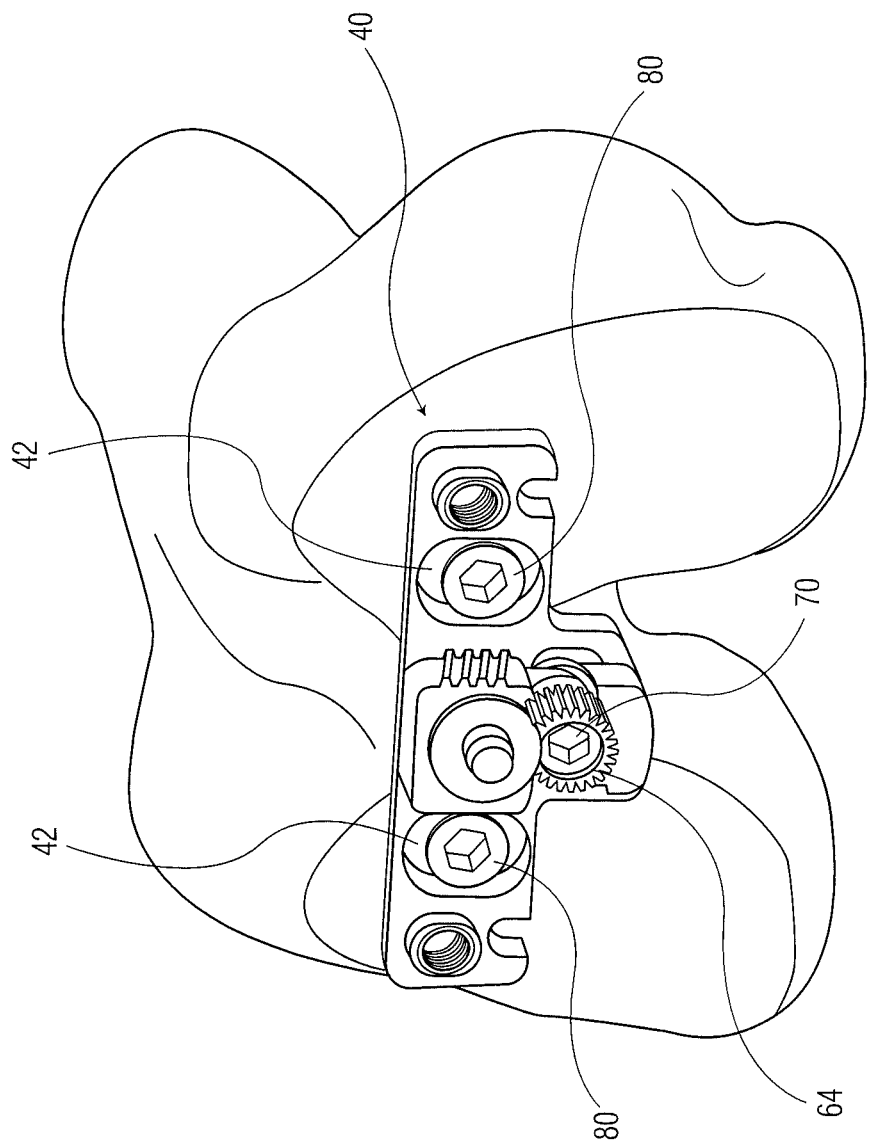
FIG. 6 is a perspective view of the drive plate shown in FIG. 4, including two guide screws mounted in slots of the drive element.

Referring to FIG. 6, there is shown the distal plate assembly 40, including a pair of screws 80 about which distal plate assembly may pivot upon rotation of spur gear 64. The kidney shape of slots 42 allows the distal plate 40 to rotate about partially inserted screws 80. This movement sets the internal/external rotation of the plate 40. Screws 80 can then be fully tightened to lock the plate in place on the distal femur.

Figure 7:
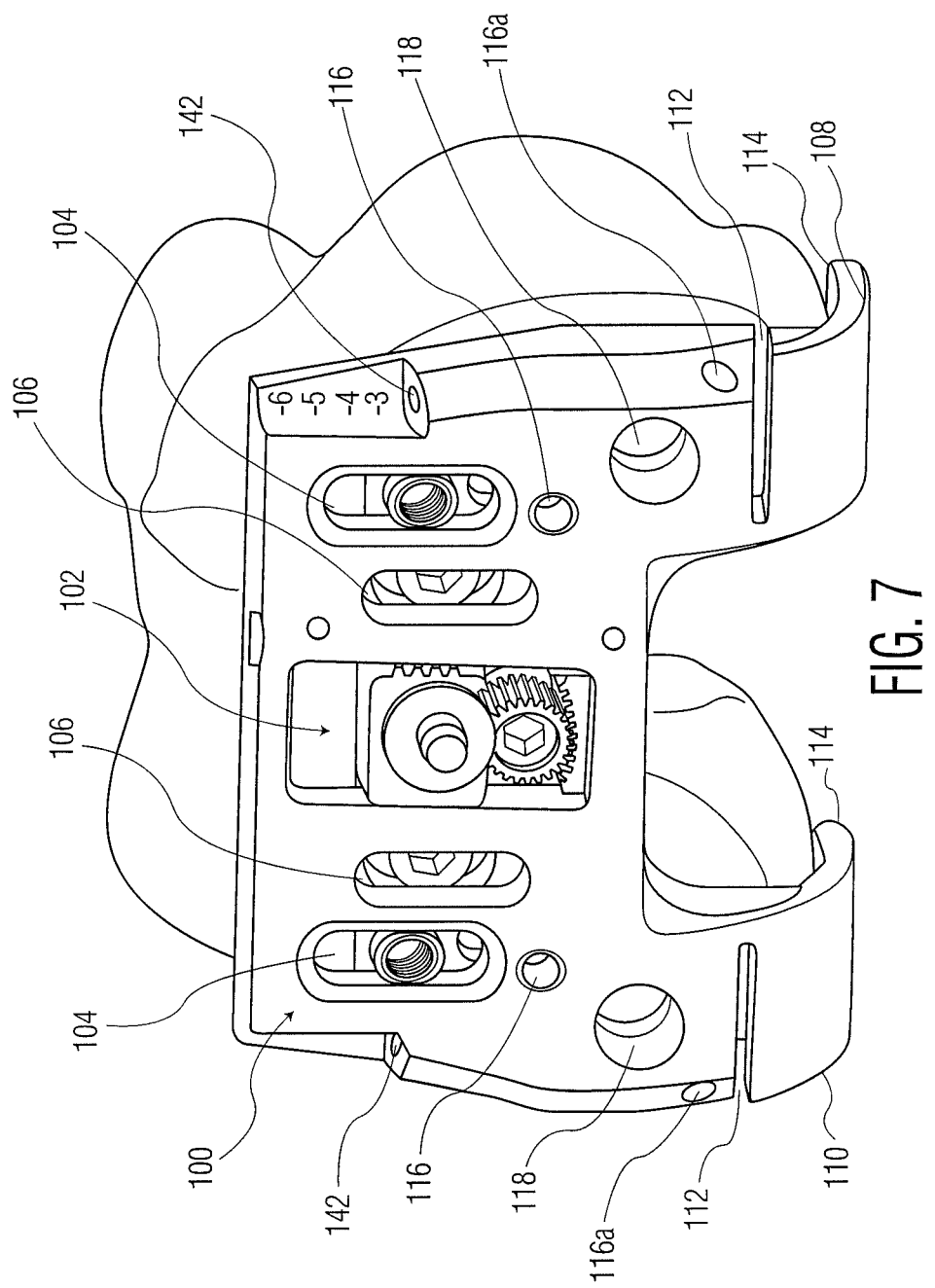
FIG. 7 is a perspective view of a ligament tensioning element mounted on the distal drive plate.

Referring to FIG. 7, there is shown a main body 100 of the gap balancing or tensioning instrument mounted on the distal plate 40. The main body 100 is shown in FIGS. 7-13. The main body includes a generally rectangular central opening 102 adapted to receive boss 54 of plate 40. Boss 54 and rectangular opening 102 are sized such that the main body may slide relative to the distal plate in the anterior-posterior direction. Main body 100 includes a pair of slots 104 both medially and laterally of the center of opening 102. Slots 104 receive mounting screws threaded into bores 44. A pair of slots 106 is also included to allow access to screws 80 located within slots 42 of distal plate 40. Also included on body 100 are medial and lateral trial condylar elements or feet 108 and 110 respectively. Each condylar element 108 and 110 includes a slot 112 extending partially therethrough from the outer edges of body 100. Preferably, the outer curved surfaces of condylar portions 108 and 110 have a constant radius from the area of slots 112 to adjacent ends 114 of each condylar portion 108, 110. This radius matches the constant radius on the prosthetic femoral component to be implanted. Main body 100 includes hole 116 to guide a drill for producing bores in the distal femur to locate the 4 in 1 cutting block for making the anterior and posterior chamfer and skin bone cuts. Main body 100 also includes holes 116a, preferably on both the lateral and medial sides of the main body to accommodate bone pins to allow the surgeon to secure the body to (100) to the distal femur during femoral preparation. The main body additionally includes bores 118 for mounting body 100 to the distal femur.

Figure 8:
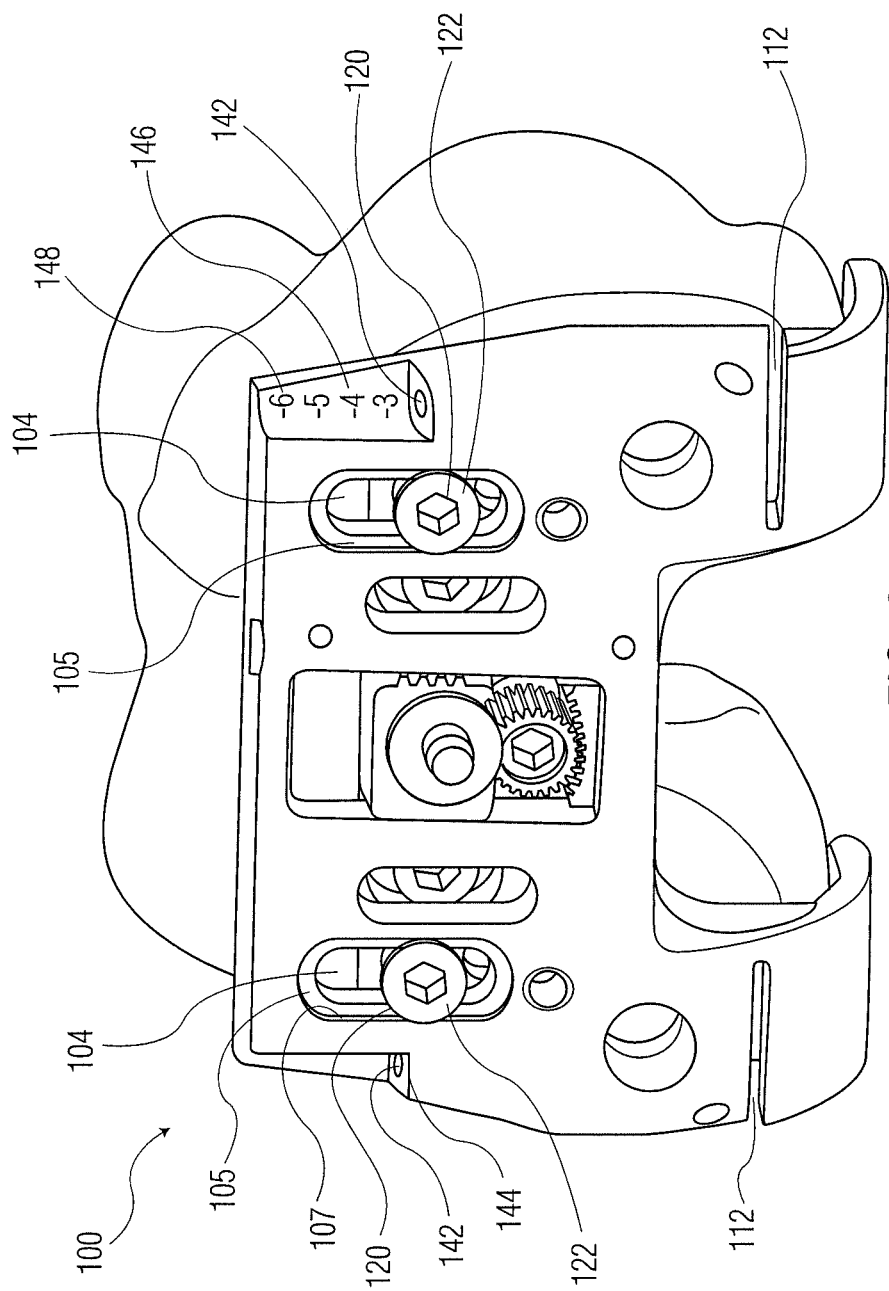
FIG. 8 shows the ligament tensioning element of FIG. 7, including two mounting screws engaging the distal plate but allowing anterior-posterior movement of the ligament tensioning element with the knee joint in the flex position.

As best seen in FIG. 8 prior to mounting the main body 100 onto the femur, screws 120 extend through slots 104 and into threaded bores 44 of distal plate assembly 40. In the preferred embodiment, the slots 104 include a recessed surface 105 to thereby form a ledge around the circumference of each slot. Screws 120 includes heads 122, which have a head with a bottom surface able to slide on ledge 105 when main body 100 is moved in the anterior-posterior direction. Heads 122 are sized such that they engage a peripheral wall 107 of the slot 104 between surface 105 and the outwardly facing surface 125 of main body 100. This helps ensure that the main body does not rotate with respect to distal plate 40 during the anterior-posterior movement which is accomplished in a manner as described below.

Figure 9:
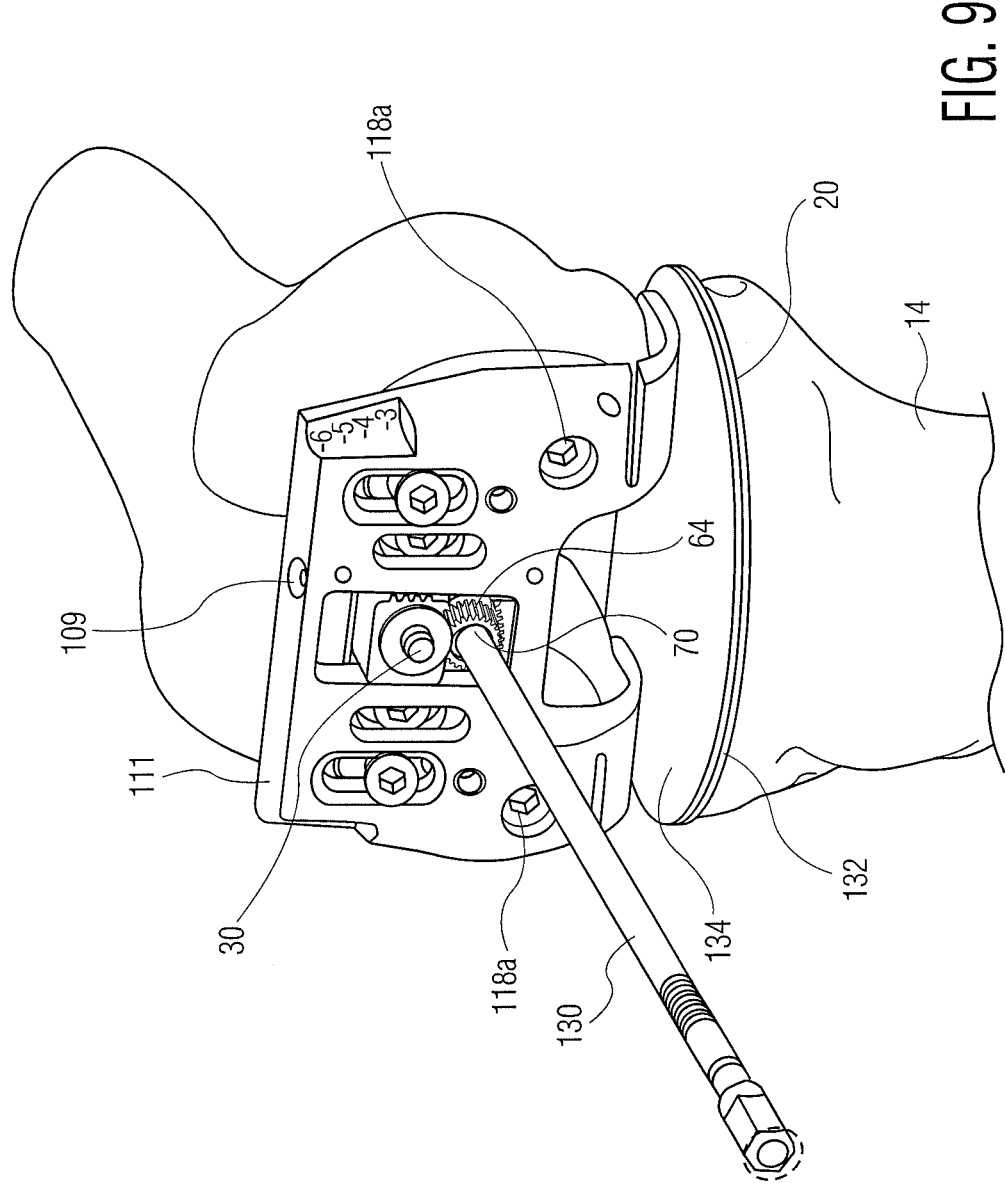
FIG. 9 shows the assembly of FIG. 8, including a drive tool for bearing the internal external rotation of the distal body with respect to the femur and including a pair of tibial shim plates engaging the outer surfaces of the medial and lateral condylar portions of the ligament tensioning element.

Referring to FIG. 9, there is shown the assembly of FIG. 8 including a drive tool 130 engaging socket 70 of spur gear 64. As indicated above, rotation of tool 130 rotates the distal plate 40 about portion 30 of intramedullary shaft 22. This movement sets the internal-external rotation of the instrument on the distal femur. Also shown in FIG. 9 are two shim plates 132, 134 located on the proximal tibial surface 20 of tibia 14. The two shim plates 132 and 134 provide a surface for the radius to articulate on in an easy manner. In the preferred embodiment, plate 132 is 2 mm and plate 134 is 4 mm such that 2, 4, and 6 mm adjustments can be possible. In use, it makes no difference whether the 2 or 4 mm plates are located on tibial surface 20 when a 6 mm correction is desired.

Figure 10:
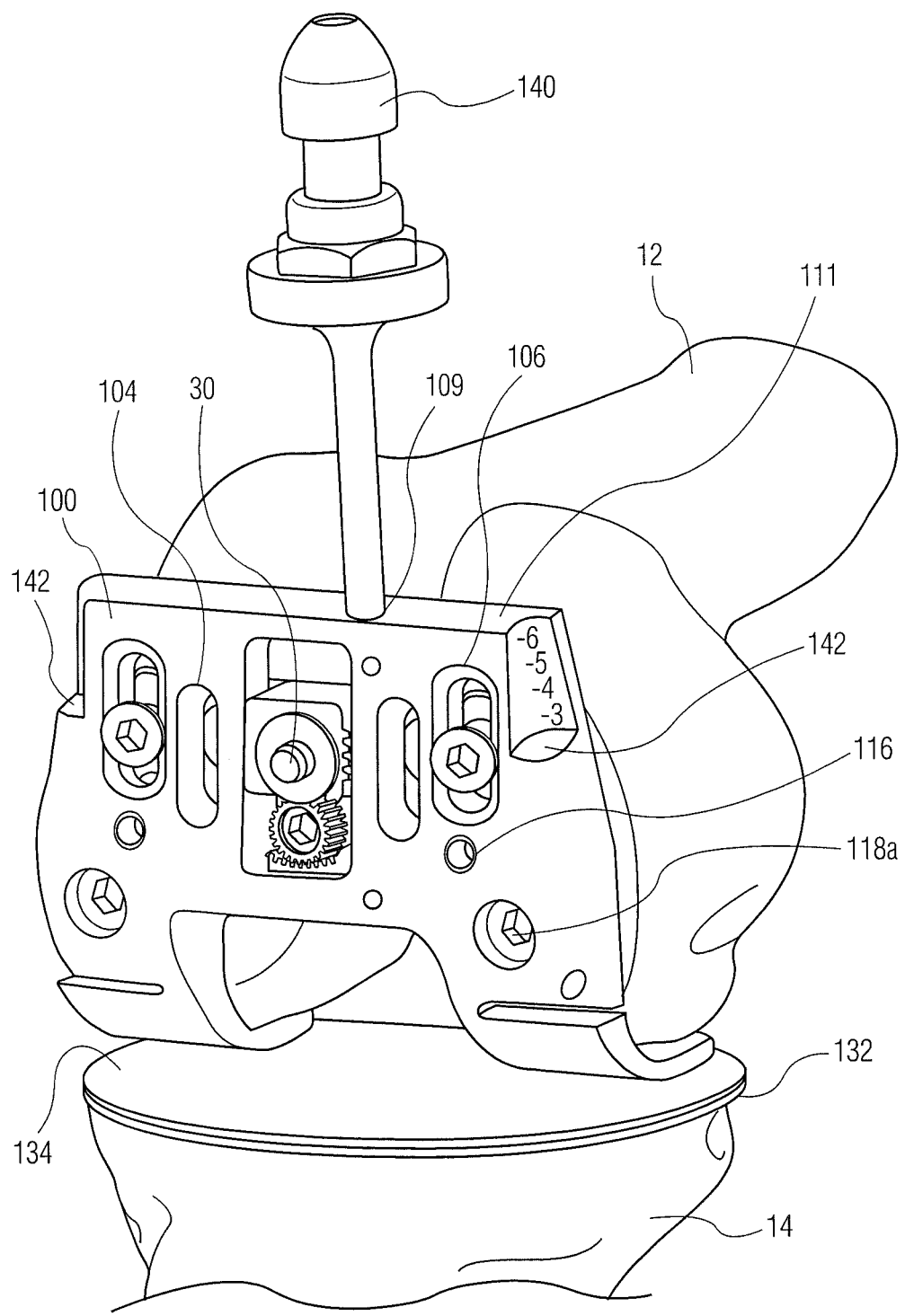
FIG. 10 is identical to FIG. 9 with the exception that the tool for changing the internal external rotation of the instrument is removed and replaced by a second tool for adjusting the anterior-posterior location of the ligament tensioning instrument on the distal femur.

Referring to FIGS. 10 and 10a, there is shown the assembly of FIG. 9, including a second drive tool 140 which drives an ACME screw 143 mounted in body 100. Screw 143 is freely rotatably mounted within a partial bore 109a in body 100 and has a drive element at an anterior end thereof open to bore 109 for engaging drive tool 140. Screw 143 has a thread for engaging the gear teeth 56 on boss 54. Tool 140 extends into bore 109 in anterior facing surface 111 of main body 100 to engage screw 143. Also shown in FIGS. 7-11 are a pair of medial and lateral blind bores 142 which extend from an anterior facing bottom surface 144 internally of the main body in a posterior direction. A surface 146 extending between bottom surface 144 and anterior surface 111 faces outwardly and includes a series of femoral component size numbers 148. Medial and lateral bores 142 are adapted to receive the shaft of a femoral component sizer generally denoted as 177 shown in FIG. 12.

Figure 11:
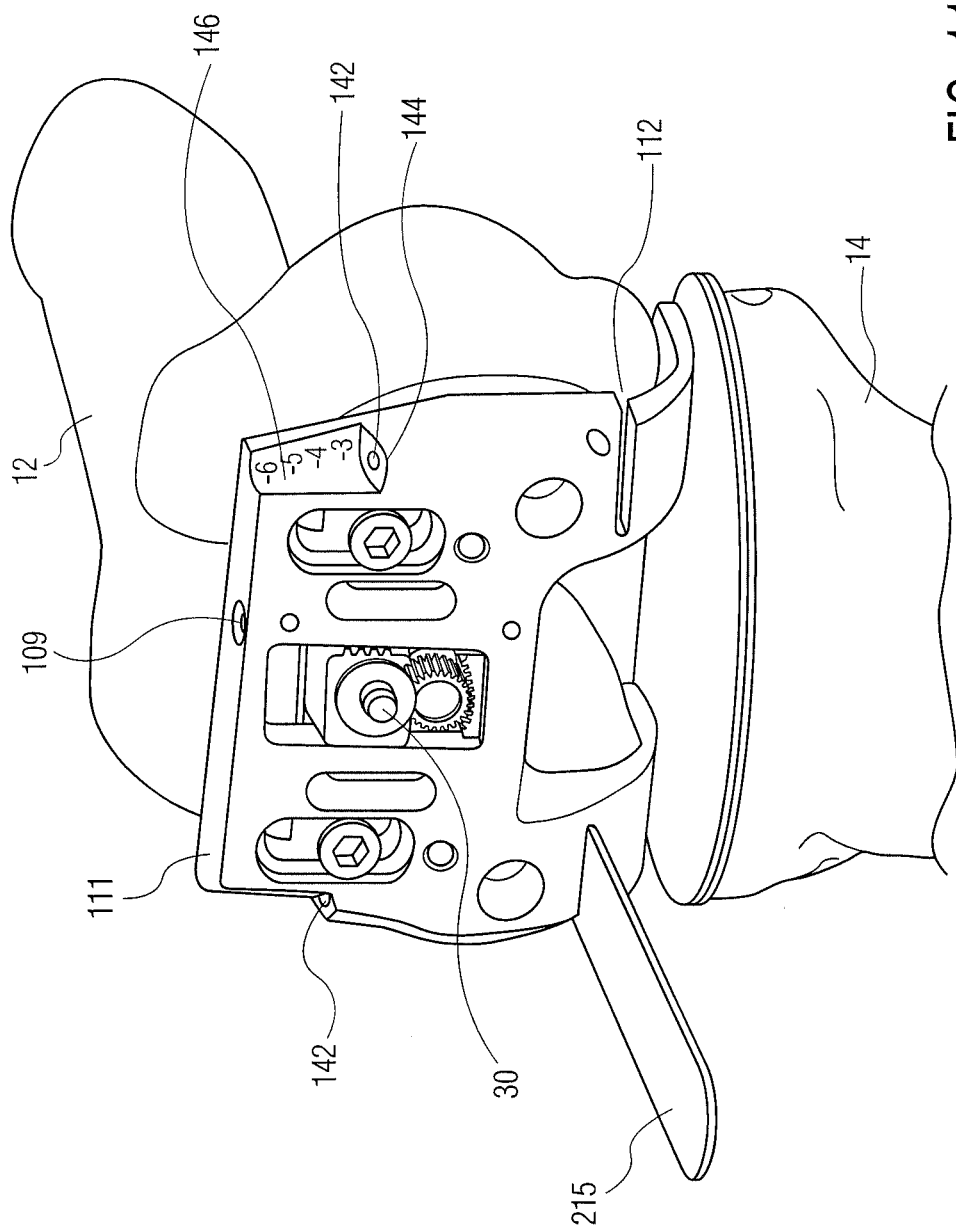
FIG. 11 is the ligament tensioning element of FIG. 10 in the position ready for ligament assessment.
Figure 12:
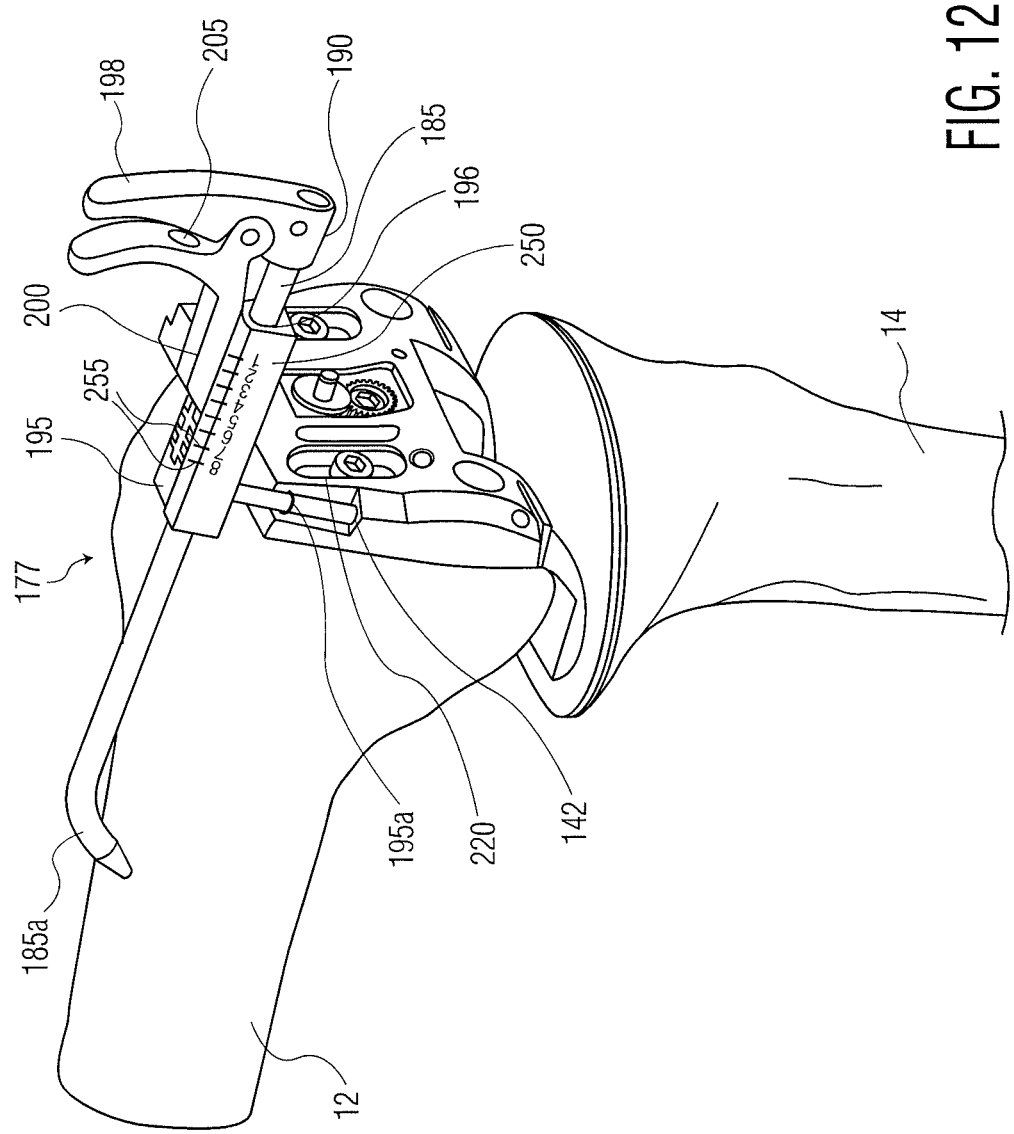
FIG. 12 is a perspective view of a ligament tensioning element including a mechanical stylus mounted on the ligament tensioning element and the stylus having a tip engaging the anterior femur.

FIG. 12 is a perspective view of an assembled sizer 177 including a mechanical stylus 180 in addition to the body 100 and module 110 of FIG. 11.

Referring to FIG. 12, the stylus includes an arm 185 with a curved tip 185a that is used for locating points on the anterior cortex of the femur 12. The stylus also includes a handle 190 that is attached to the arm and a stylus body 195 that is attached to a shaft or rod 195a. Bore 142 accommodates shaft or rod 195a such that the stylus 185 is free to rotate about the longitudinal axis of rod 195a and is free to translate longitudinally such that the stylus may move in a direction along the hole 142 longitudinal axis. The handle 190 can be used to translate the arm within a bore in stylus body 195 through a hole 196 in a direction parallel to the stylus body 195 longitudinal axis. This is in the proximal-distal direction. Handle 196 can also be used to rotate the arm about the arm's longitudinal axis if necessary. A latch 200 is provided for locking the arm in a desired translation position and in the rotation position in which the handle is in a generally aligned with the longitudinal axis of rod 195a. The latch is spring loaded with respect to the handle by a spring 205. To release the latch, finger pressure is applied to the latch so as to compress the spring allowing arm 185 to be moved.

Notably, the orientation of lever 198 of handle 190 in the proximal direction is advantageous. Orienting lever 198 as shown in FIG. 12 facilitates manipulation of the stylus during knee arthroplasty by positioning the handle away from the incision area.

A further indication of implant size is provided by a superior-inferior run-out scale ("SI scale") 250. The SI scale is associated with a multiple of notches 255 that are etched into the stylus body, each notch being associated with a corresponding size. When the curved tip of the stylus has been located at the desired run-out point, the latch is allowed to settle into the notch that most closely corresponds to the stylus position. The number associated with the notch into which the latch settles is the femur/implant size as measured by the SI scale. For example, if the latch sits in the notch corresponding to the number "3" of SI scale, then the SI scale indicates a femur/implant size "3."

The sizer of FIG. 12 is used to determine correct implant size and cutting block pin position by referencing the posterior condyles of the distal femur. More specifically, the sizer is aligned with the posterior condylar axis through this two condylar skids 108 and 110 located on the base of the tensioned body 100. The skids 108,110 are positioned to contact the posterior condyles while the body is centered, or approximately centered, on the femur with respect to the medial-lateral direction.

Figure 13:
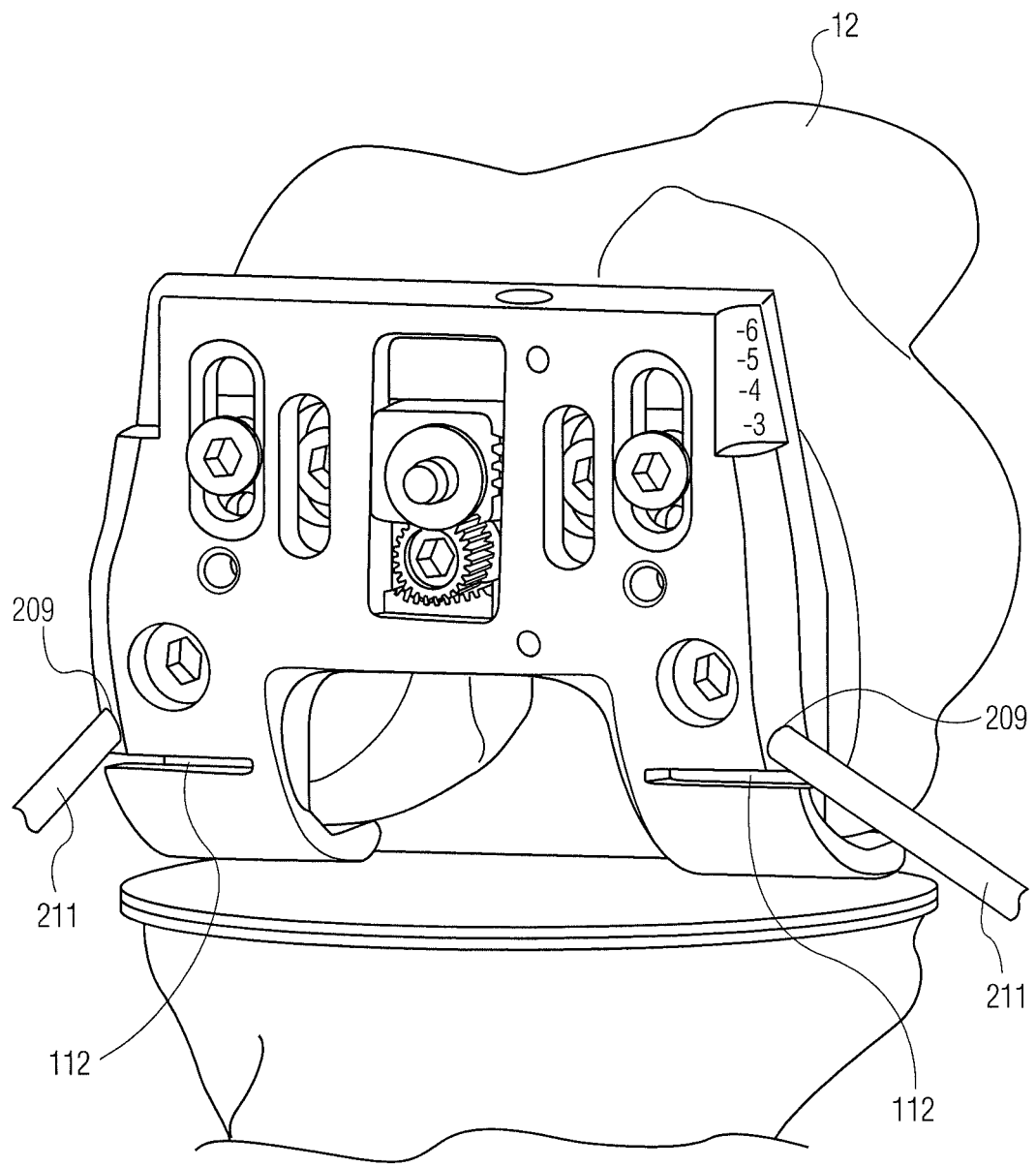
FIG. 13 shows the ligament tensioning element in its final position with a pair of cutting slots respectively aligned with the medial and lateral posterior condyles.

FIG. 13 shows the guide mounted on the distal femur just prior to resecting the posterior condyle prior to resecting the posterior condyle via slots 112. Bores 209 are provided to allow the use of pins 211 to hold the guide on femur 12.

Once the body is properly positioned, pins can be passed through either one pair of pinholes 116 or 116a, or through both pairs of pinholes 116 and 116a, to secure the body to the femur. In a preferred embodiment, the body 100, and stylus 180 are removably attached to each other to form a complete assembly, and then the complete assembly is attached to the femur via the pinholes.

Figure 14:
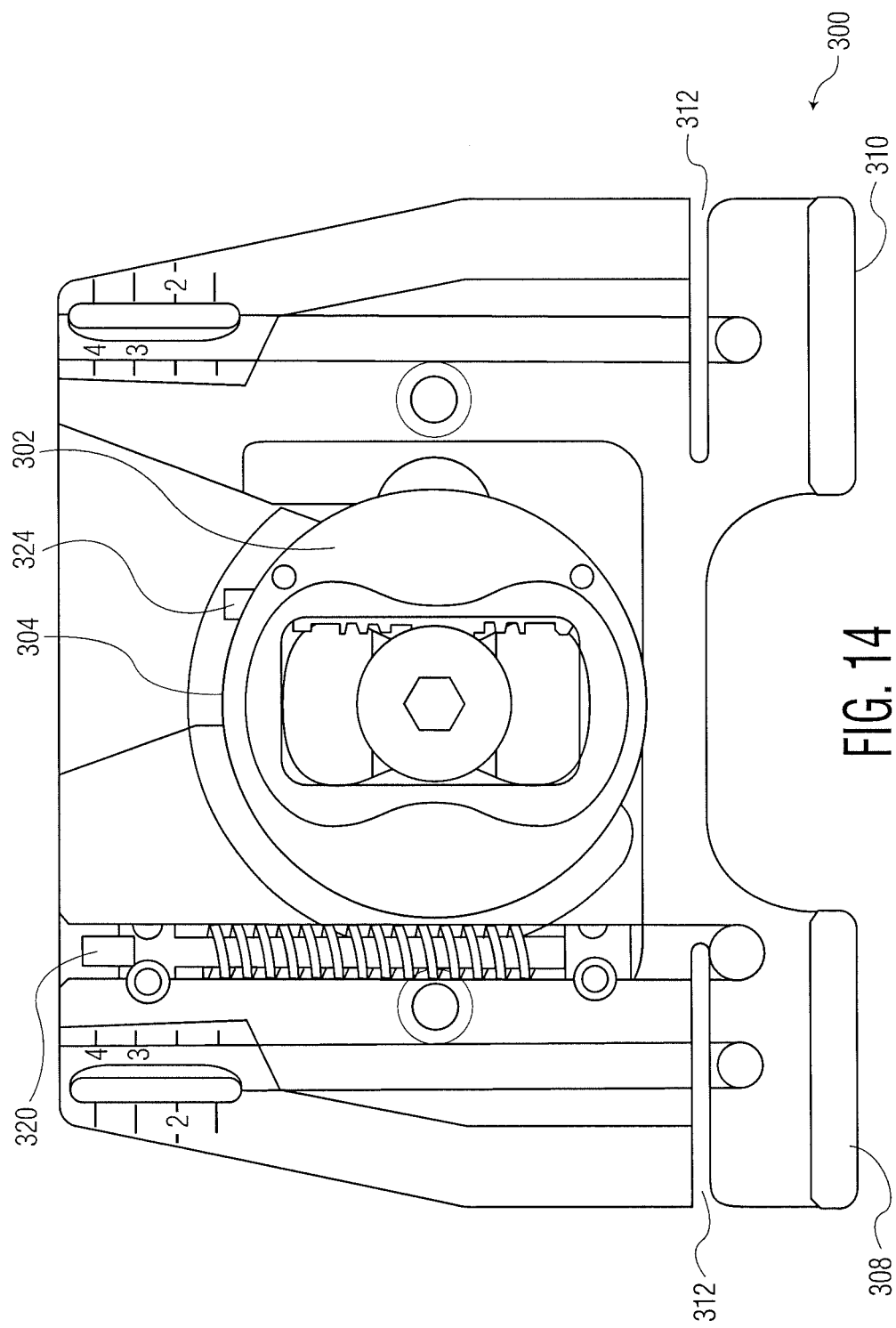
FIG. 14 is a view of the distally facing surface of an alternate main body of a gap balancing or tensioning instrument.
Figure 15:
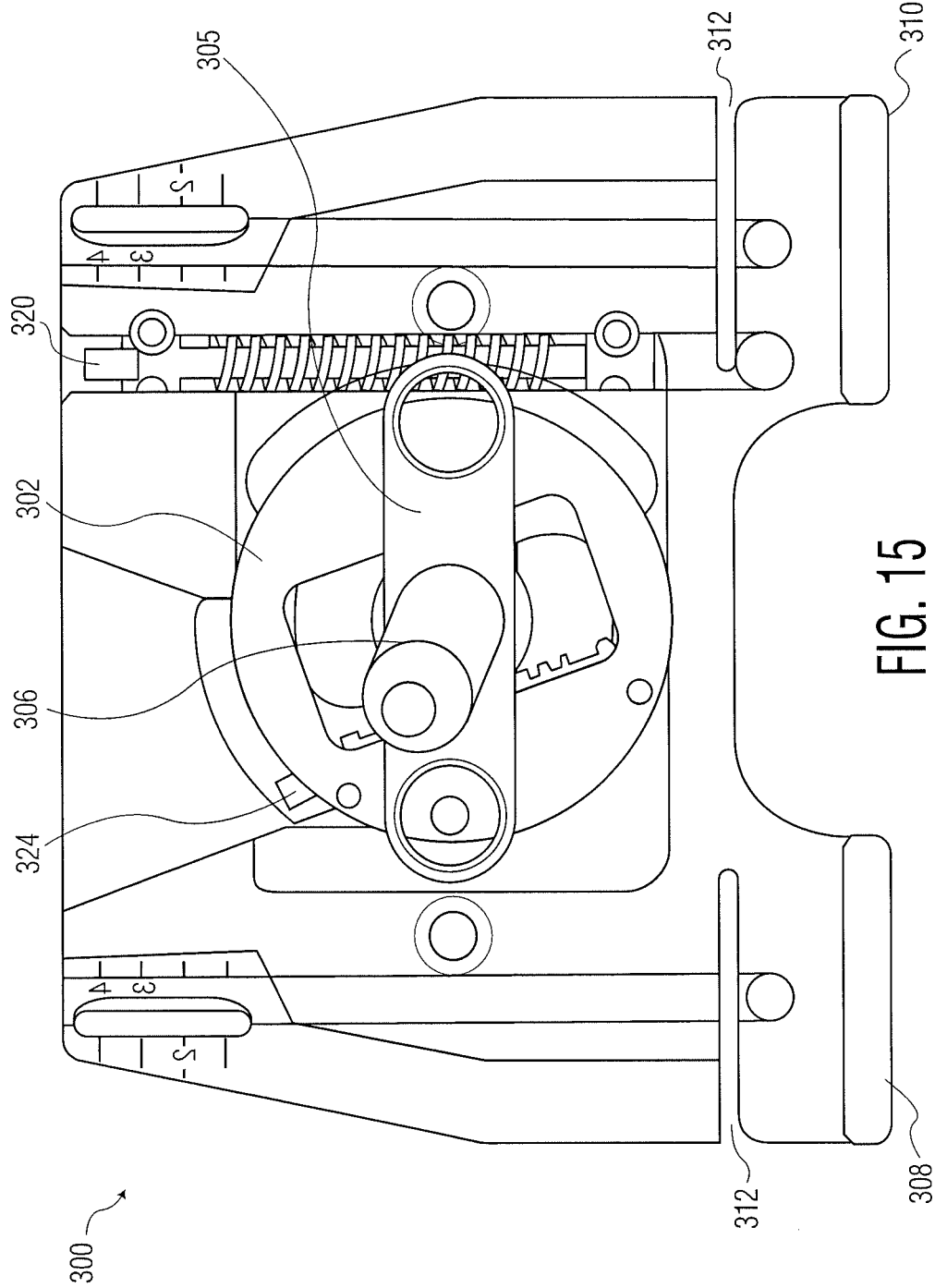
FIG. 15 is a view of the main body of the alternate gap balancing or tensioning instrument as shown in FIG. 1 showing the proximally facing side.
Figure 16:
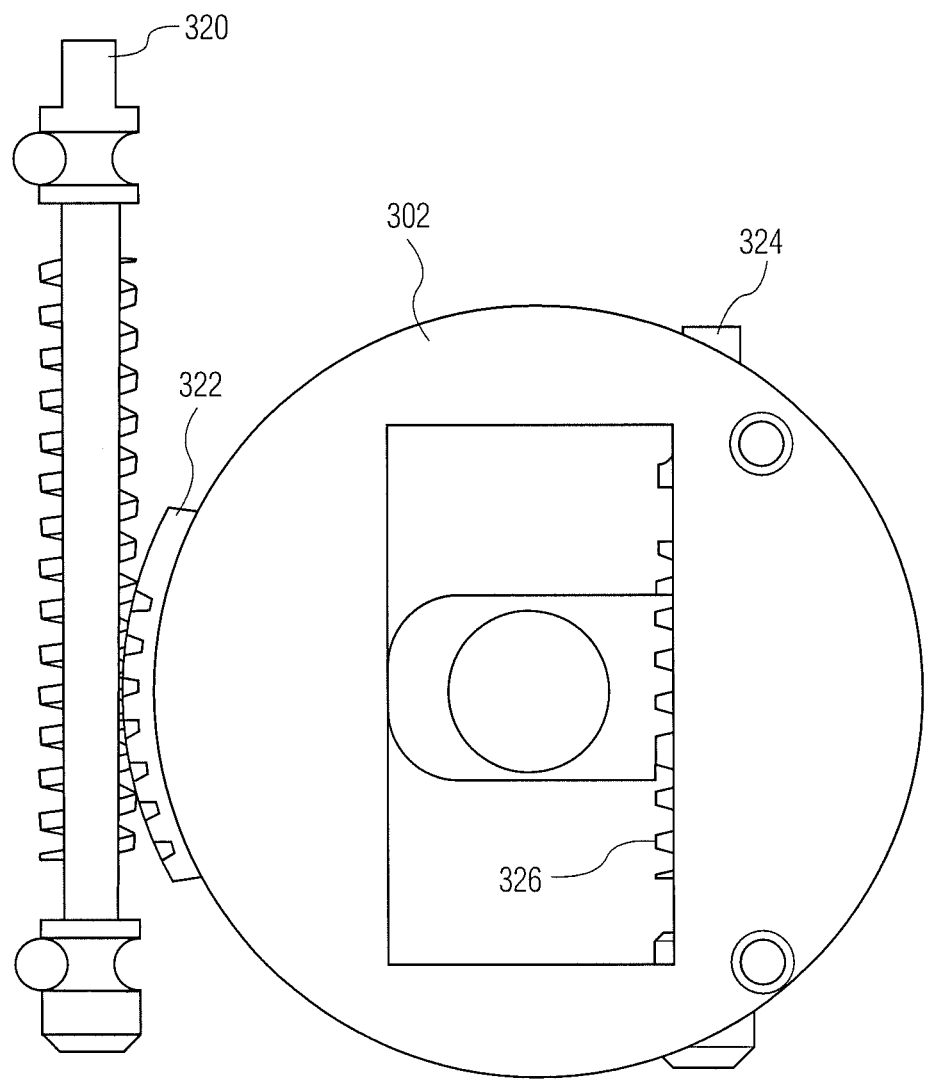
FIG. 16 is a partial view of the mechanism which moves the alternate body of the gap balancing and tensioning instrument in the anterior-posterior direction and rotates the body in internal/external rotation.

Referring to FIGS. 14-16 there is shown an alternate embodiment of a main body 300 for the instrument of the present invention. Main body 300 is similar to main body 100 with the main exception being the rotational mechanism shown in FIG. 16. Referring to FIGS. 14 and 15 body 300 includes a rotating disk 302 mounted in a bore 304 therein. As shown in FIG. 15 the proximally facing side of body 300 has a plate 305 mounted on disk 302. Plate 305 is initially mounted on the distal femur and includes an intramedullary rod portion 306 for insertion into the intramedullary canal of the femur. As with body 100 body 300 includes a pair of condylar portions 308 and 310 and slots 312. As with body 100 body 300 includes a drive screw system for adjusting the body including a screw 320 mounted in body 300 for engaging a circular gear segment 322 fixed to disc 302. This is best seen in FIG. 16. A screw element or rack element 324 having teeth 326 is mounted within disk 302 for engaging teeth 56 on plate 40 as shown in FIG. 5. Thus rotation of screw 324 causes movement of body 300 in a proximal-distal direction while rotation of screw 320 causes internal and external rotation of body 300 about the axis of rod 306. This design works the same way as that described below for body 100, the main difference being the change in location of the internal/external rotation drive gear 322 on disk 302.

The use of the instrument assembly including body 100 set forth above will now be described. Initially the surgeon drills a hole into the intramedullary canal of the distal femur. The surgeon then inserts intramedullary rod 22 such that portion 30 thereof extends distally of the prepared surfaces 16 and 18 of femur 12. The surgeon then assembles distal plate 40 onto the distal femur over portion 30 of IM rod 22. The surgeon sets distal plate 40 at the approximate internal/external rotational position that is desired. The plate is then secured to the distal femur by means of bone screws 80. Main body 100 is then placed over distal plate 40. Posterior condylar feet 108, 110 on main body 100 are placed under the posterior condyles of the femur. Main body 100 is secured to distal plate 40 by means of screws 120. Screws 120 secure main body 100 to distal plate 40 but allow main body 100 to move in an anterior-posterior direction by means of adjustment screw 140. The surgeon then performs a trial reduction with the instrument in place.

Trial reduction takes place by means of the offset single radius on the periphery of condylar skids 108, 110. The surgeon places a tibial shim plate (2, 4, or 6 mm) 132, 134 on the proximal tibia. This plate acts as a protective plate for the resected bone on the tibia and also as a firm surface for the condylar skids of the main body 100 to articulate on. The surgeon then puts the knee through a range of motion and assesses stability throughout the complete range. The surgeon has multiple thickness spacer blocks which allow the surgeon to assess the gap (if any) on each condyle.

If the surgeon establishes that adjustment is required, then the following steps can be taken. If internal/external rotation adjustment is required then the surgeon opens (not removes) bone screws 80 from the distal plate and places drive tool 130 into spur gear 64 and rotates the distal plate 40 until the desired position has been obtained. The surgeon can then resecure the distal plate at this position if desired. However, the surgeon can adjust the AP position by means of actuating tool 140 to drive the acme screw. Once the desired internal/external rotation of the main body 100 has been achieved, distal plate 40 is secured to the femur. The surgeon then begins the process of assessing the resection levels and the femoral component size. The resection level is assessed by means of a blade runner shown in FIG. 11 placed into slots 112 of both condyles 108, 110, and by placing the stylus into one of the holes or bores 142.

After the internal-external rotation and anterior-posterior location of the implant is set, the stylus can be used to size the femur. That is, the stylus can be used to determine the appropriate size implant needed for the subject femur. To size the femur, a practitioner manipulates the stylus handle such that the curved tip 185a of the stylus contacts the anterior cortex of the femur at the point where the anterior-superior point of the implant should contact the anterior cortex of the femur (the "desired run-out point"). Once the tip is contacting the desired run-out point, the practitioner reads the size from an anterior-posterior sizing scale ("AP scale") 148 located on surface 146. The reading is taken by comparing a ring 220 on the stylus 195a to the AP scale. For example, if the ring is aligned toward the number "3" of the AP scale 148, then the femur size is a "3" and the implant needed is a size "3." The sizes may be femoral component sizes 1-8 of the Triathlon® line of implants.

Finally, the surgeon drills two holes through bores 116 on the distal femur. The two bores 116 position a standard 4-in-1 cutting guide in the correct position so that the remaining cuts (anterior and posterior chamfer and skim cuts) can be made on the distal femur.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An instrument system for setting ligament tension between a distal femur and a proximal tibia during total knee arthroplasty, comprising
    a rod for mounting in an intramedullary canal of a distal femur, the rod having an extension portion extending outwardly of the distal femur along a first axis;
    a first drive element mounted on the rod portion extending from the distal femur and rotatable about a second axis parallel to and offset from the first axis;
    a body rotatably mounted on the extension portion of the rod for rotation about the first axis, the body having a second drive element engaging the first drive element whereby rotation of the first drive element about the second axis rotates the body with respect to the first axis, the body further comprising a third drive element extending about a third axis offset from the first and second axis;
    a ligament tensioning element mounted on the body for movement with respect thereto, the ligament tensioning element having a foot for engaging a posterior condyle of a femur and having a fourth drive element extending generally parallel to and spaced from the third drive element; and
    a fifth drive element engaging both the third and fourth drive elements for moving the ligament tensioning element with respect to the body along the third axis.

2. The instrument system as set forth in claim 1, wherein the first drive element is a gear having teeth meshing with teeth on the second drive element.

3. The instrument system as set forth in claim 2, wherein the third and fourth drive elements are a plurality of teeth and the fifth drive element is a screw operatively engaging the teeth.

4. The instrument system as set forth in claim 1, wherein the ligament tensioning element has a first foot for engaging a posterior surface of a medial condyle and a second foot for engaging a lateral condyle of a femur.

5. The instrument system as set forth in claim 4, wherein the first and second feet have outer surfaces for contacting a tibial surface, the outer surfaces having a portion with a constant radius in a saggital plane.

6. The instrument system as set forth in claim 1, wherein the body includes first and second elongated slots elongated along an axis parallel to the third axis.

7. The instrument system as set forth in claim 6, wherein the system further comprises a pair of screws extending through the first and second slots of the body for mounting the body to a planar surface on the distal femur.

8. The instrument system as set forth in claim 1, wherein the body includes a first threaded bore on a medial side of the body and a second threaded bore on a lateral side of the body.

9. The instrument system as set forth in claim 8, wherein the ligament balancer has first and second elongate openings respectively aligned with the first and second threaded bores in the body, and the system further comprises first and second screws extending respectively through the first and second slots and threaded into the first and second bores for mounting the ligament balancer to the body.

10. The instrument system as set forth in claim 9, wherein the elongated slots have elongated portions extending along axes parallel to the third axis.

11. The instrument system as set forth in claim 10 further comprising a femoral sizing module mounted on the ligament balancer, the femoral sizing module moveable in an anterior-posterior direction with respect to the balancer and stylus slidably mounted on the module for movement in a proximal distal direction and having a tip for contacting an anterior surface of the distal femur.

12. An instrument system for setting ligament tension between a distal femur and a proximal tibia during total knee arthroplasty, comprising
 a plate rotatably mounted on a resected planar distal surface of a femur for rotation about a first axis;
 a ligament tensioning element mounted on the plate for rotation therewith about the first axis and for movement with respect to the plate in a plane parallel to the resected planar surface of the femur, the plate having a foot for engaging a posterior surface of the distal femur;
 a means for rotating the plate and ligament tension about the first axis;
 a means for moving the tensioning element with respect to the plate in the plane in a generally anterior-posterior direction of the distal femur; and
 means for locking the ligament tensioning element in a desired location with respect to the distal femur.

13. The instrument as set forth in claim 12 further comprising an intramedullary rod having a first portion aligned with a longitudinal axis of the femur and a second portion angled with respect to the first portion extending along the first axis.

14. The instrument as set forth in claim 13, wherein the angle between the first and second rod portions is between 3° and 6°.

15. The instrument as set forth in claim 13, wherein the second portion comprises anti-rotation elements extending radically outwardly from the first axis.

16. The instrument as set forth in claim 13, wherein the means for rotating the plate and ligament about the first axis comprises a gear body having a bore engaging the second portion of the rod, the bore having a central axis coaxial with the first axis and a gear element rotatable with respect to the gear body about a third axis parallel to the first axis, the gear element having teeth operatively engaging a portion of the plate having teeth.

17. The instrument as set forth in claim 16, wherein the plate includes an opening for receiving the gear body, the opening sized to permit the plate to rotate ±5° about a saggital plane bisecting the resected distal femur.

* * * * *